(12) United States Patent
Cardinal et al.

(10) Patent No.: US 12,133,871 B2
(45) Date of Patent: Nov. 5, 2024

(54) METHODS AND COMPOSITIONS TO ENHANCE ARTERIOGENESIS

(71) Applicant: Cal Poly Corporation, San Luis Obispo, CA (US)

(72) Inventors: Trevor Cardinal, San Luis Obispo, CA (US); Vahid Hamzeinejad, San Diego, CA (US); Ethan Tietze, Baltimore, MD (US)

(73) Assignee: Cal Poly Corporation, San Luis Obispo, CA (US)

( * ) Notice: Subject to any disclaimer, the term of this patent is extended or adjusted under 35 U.S.C. 154(b) by 1130 days.

(21) Appl. No.: 16/852,081

(22) Filed: Apr. 17, 2020

(65) Prior Publication Data
US 2020/0330521 A1    Oct. 22, 2020

Related U.S. Application Data

(60) Provisional application No. 62/836,267, filed on Apr. 19, 2019.

(51) Int. Cl.
*A61K 35/34* (2015.01)
*A61P 9/00* (2006.01)
*G01N 33/68* (2006.01)

(52) U.S. Cl.
CPC .............. *A61K 35/34* (2013.01); *A61P 9/00* (2018.01); *G01N 33/6893* (2013.01)

(58) Field of Classification Search
CPC ............................ A61K 35/34; C12N 5/0658
See application file for complete search history.

(56) References Cited

U.S. PATENT DOCUMENTS

2008/0200899 A1* 8/2008 McIntosh ............... A61K 38/18
623/1.42

OTHER PUBLICATIONS

Christofferson et al. "Effect of Chronic Total Coronary Occlusion on Treatment Strategy" The American Journal of Cardiology vol. 95, May 1, 2005, pp. 1088-1091 (Year: 2005).*
Darvall et al. "Obesity and Thrombosis" Eur J Vasc Endovasc Surg 33, pp. 223-233 (2007) (Year: 2007).*
Wang 2012 "Genetic Dissection of the Canq1 Locus Governing Variation in Extent of the Collateral Circulation" PLoS ONE, Mar. 2012, vol. 7, Issue 3, 13 pages (Year: 2012).*
Wang 2016 "Genetic Dissection of Cardiac Remodeling in an Isoproterenol-Induced Heart Failure Mouse Model" PLOS Genetics Jul. 6, 2016, 30 pages (Year: 2016).*
NIH "Calculate Your Body Mass Index" available online at www.nhlbi.nih.gov/healthleducational/lose_wt/BMI/bmicalc.htm on Jan. 1, 2015 (Year: 2015).*
Mayo Clinic "Peripheral artery disease (PAD)" p. 11, © 1998-2024 (Year: 1998).*
Okeke et al. "Role of genetics in peripheral arterial disease outcomes; significance of limb-salvage quantitative locus-1 genes" Experimental Biology and Medicine 2018; 243: 190-197, 8 pages (Year: 2017).*
Tran et al "The Impact of Primary Myoblast Transplantation on Functional Vasodilation Following Arteriogenesis in Mice with DietInduced Obesity" vol. 32, Issue S1 Experimental Biology 2018 Meeting Abstracts, Apr. 1, 2018 pp. 573.10-573.10 (Year: 2018).*
Shahini et al. "Efficient and high yield isolation of myoblasts from skeletal muscle" Stem Cell Res. Jul. 2018 ; 30: 122-129 (Year: 2018).*
Meligy et al. "The efficiency of in vitro isolation and myogenic differentiation of MSCs derived from adipose connective tissue, bone marrow, and skeletal muscle tissue" In Vitro Cell. Dev. Biol.—Animal (2012) 48:203-215 (Year: 2012).*
Hansen et al., "Abstract 317: Paracrine Effects of Satellite Cells on Collateral Vessel Formation", Arteriosclerosis, Thrombosis, and Vascular Biology, vol. 36, 6 pages, Feb. 9, 2017.
Jansen et al., "Abstract 317: Satellite Cells Influence Collateral Vessel Formation via Paracrine Effects", Arteriosclerosis, Thrombosis, and Vascular Biology, vol. 37, 6 pages, Aug. 25, 2017.
Hansen et al., Abstract 18683: Satellite Cells are a Major Source of the Receptor for Advanced Glycation End Products in the Ischemic Leg and Play a Role in Collateral Growth, Circulation, vol. 130, 6 pages, Mar. 27, 2018.
Hansen et al., "Abstract 649: Skeletal Muscle Satellite Cells Play a Role in Regulating Angiogenesis and Arteriogenesis", Arteriosclerosis, Thrombosis, and Vascular Biology, vol. 38, 6 pages, Mar. 12, 2019.
Hansen et al., "Abstract 635: Satellite Cells Play a Role in Revascularization of Ischemic Tissue", Arteriosclerosis, Thrombosis, and Vascular Biology, vol. 39, 6 pages, Jul. 19, 2019.
Joseph et al., "Abstract MP152: Satellite Cell Expression of Rage is Important for Collateral Vessel Formation", Arteriosclerosis, Thrombosis, and Vascular Biology, vol. 40, 6 pages, Jun. 29, 2020.
Aharinejad et al., "Colony-stimulating factor-1 transfection of myoblasts improves the repair of failing myocardium following autologous myoblast transplantation", Cardiovascular Research, vol. 79, pp. 395-404, Apr. 10, 2008.
Arnold et al., "Inflammatory monocytes recruited after skeletal muscle injury switch into antiinflammatory macrophages to support myogenesis", JEM, vol. 204, No. 5, pp. 1057-1069, May 14, 2007.
Christov et al., "Muscle Satellite Cells and Endothelial Cells: Close Neighbors and Privileged Partners", Molecular Biology of the Cell, vol. 18, pp. 1397-1409, Apr. 2007.
Ciecierska et al., "Myogenic Cells Applications in Regeneration of Post-Infarction Cardiac Tissue", Journal of Physiology and Pharmacology, vol. 64, No. 4, pp. 401-408, 2013.

(Continued)

*Primary Examiner* — Thane Underdahl
(74) *Attorney, Agent, or Firm* — McKee, Voorhees & Sease, PLC

(57) ABSTRACT

A method is described for enhancing arteriogenesis in animals with comorbidities commonly found in patients with ischemic disease, and in animals with a genetically-impaired arteriogenesis response. Administration to an animal of satellite derived myoblasts increases maximum diameter of collateral arteries. In embodiments, the animal is an obese animal or an animal having impaired arteriogenesis due to genetic variation causing the phenotype. The administration of such myoblasts to a non-obese animal does not increase maximum diameter of the animal's collateral arteries. Blood flow is increased, and ischemia is decreased. Compositions and kits comprising the myoblasts are also provided.

19 Claims, 6 Drawing Sheets
(5 of 6 Drawing Sheet(s) Filed in Color)

(56) References Cited

OTHER PUBLICATIONS

Clayton et al., "Vascular Endothelial Growth Factor-A Specifies Formation of Native Collaterals and Regulates Collateral Growth in Ischemia", Circ. Res., vol. 103(9), pp. 1027-1036, Oct. 24, 2008.
Della Vedova et al., "A Mouse Model of Diet-Induced Obesity Resembling Most Features of Human Metabolic Syndrome", Livertas Academica, Freedom to Research, 9, pp. 93-102, Nov. 2, 2016.
Gilbert, S. F, "Paracrine Factors", Developmental Biology, 6th edition, Chapter 6, 6 pages, 2000.
Ding et al., "Mesenchymal stem cells in rabbit meniscus and bone marrow exhibit a similar feature but a heterogeneous multi-differentiation potential: superiority of meniscus as a cell source for meniscus repair", BMC Musculoskeletal Disorders, 16:65, 14 pages, 2015.
Fuchs et al., "Socializing with the Neighbors: Stem Cells and Their Niche", Cell, vol. 116, pp. 769-778, Mar. 19, 2004.
Heil et al., "Blood monocyte concentration is critical for enhancement of collateral artery growth", Am. J. Physiol. Heart Circ. Physiol., vol. 283, pp. H2411-H2419, Aug. 2, 2002.
Horsley et al., "IL-4 Acts as a Myoblast Recruitment Factor during Mammalian Muscle Growth", Cell, vol. 113, pp. 183-494, May 16, 2003.
Latroche et al., "Coupling between Myogenesis and Angiogenesis during Skeletal Muscle Regeneration is Stimulated by Restorative Macrophages", Stem Cell Reports, vol. 9, pp. 2018-2033, Dec. 12, 2017.
Meligy et al., "The efficiency of in vitro isolation and myogenic differentiation of MSCs derived from adipose connective tissue, bone morrow, and skeletal muscle tissue", In Vitro Cell Dev. Biol.—Animal, 13 pages, Jan. 19, 2012.
Norgren et al., "Inter-Society Consensus for the Management of Peripheral Arterial Disease (TASC II)", Eur. J. Vasc. Endovasc. Surg., vol. 33, Supplement 1, 75 pages, 2007.
Okeke et al., "Role of genetics in peripheral arterial disease outcomes; significance of limb-salvage quantitative focus-1 genes", Experimental Biology and Medicine, vol. 243, pp. 190-197, 2018.
Patsalos et al., "In situ macrophage phenotypic transition is affected by altered cellular composition prior to acute sterile muscle injury", J. Physiol., vol. 595.17, pp. 5815-5842, 2017.
Peeters Weem et al., "Bone Marrow derived Cell Therapy in Critical Limb Ischemia: A Meta-analysis of Randomized Placebo Controlled Trials", Eur. J. Endovasc. Surg., vol. 50, pp. 775-783, 2015.
Renault et al., "Gli3 Regulation of Myogenesis Is Necessary for Ischemia-Induced Angiogenesis", Circ. Res., vol. 113(10), pp. 1148-1158, Oct. 25, 2013.
Rhoads et al., "Satellite cells isolated from aged or dystrophic muscle exhibit a reduced capacity to promote angiogenesis in vitro", Biochemical and Biophysical Research Communications, vol. 440, pp. 399-404, Aug. 28, 2013.
Rhoads et al., "Satellite cell-mediated angiogenesis in vitro coincides with a functional hypoxia-inducible factor pathway", Am. J. Physiol. Cell Physiol., vol. 296(6), pp. C1321-C1328, Jun. 2009.
Rong et al., "Transplantation of HGF gene-engineered skeletal myoblasts improve infarction recovery in a rat myocardial ischemia model", PLOS ONE, 19 pages, May 1, 2017.
Saclier et al., "Monocyte/macrophage interactions with myogenic precursor cells during skeletal muscle regeneration", FEBS Journal, vol. 280, pp. 4118-4130, Jan. 31, 2013.
Snijders et al., "Satellite cells in human skeletal muscle plasticity", Frontiers in Physiology, vol. 6, Article 283, 21 pages, Oct. 2015.
Wang et al., "Genetic Dissection of the Canq1 Locus Governing Variation in Extent of the Collateral Circulation", vol. 7, Issue 3, 13 pages, Mar. 2012.
Wang et al., "Genetic Architecture Underlying Variation in Extent and Remodeling of the Collateral Circulation", Circ. Res., vol. 107(4), pp. 558-568, Aug. 20, 2010.
Yablonka-Reuveni, Zipora, "The Skeletal Muscle Satellite Cell: Still Young and Fascinating at 50", Journal of Histochemistry and Cytochemisty, vol. 59(12), pp. 1041-1059, 2011.
Lee et al., "Genetically Engineered Myoblast Sheet for Therapeutic Angiogenesis", BioMacromolecules, vol. 15, pp. 361-372, 2014.
Palmieri et al., "Past, present and future of myoblast transplantation in the treatment of Duchenne muscular dystrophy", Pediatric Transplantation, vol. 14, pp. 813-819, 2010.
Vinarov et al., "Cell therapy for stress urinary incontinence: Present-day frontiers", J. Tissue Eng. Regen. Med., vol. 12, 14 pages, 2018.
Rao et al., "Engineering an Injectable Muscle-Specific Microenvironment for Improved Cell Delivery Using a Nanofibrous Extracellular Matrix Hydrogel", ACS Nano., vol. 11(4), pp. 3851-3859, Apr. 25, 2017.

* cited by examiner

METHODS AND COMPOSITIONS TO ENHANCE ARTERIOGENESIS

REFERENCE TO RELATED APPLICATION

This application claims the benefit of and priority to previously filed application U.S. Ser. No. 62/836,267, filed Apr. 19, 2019, the contents of which are incorporated herein by reference in its entirety.

BACKGROUND

Critical limb ischemia (CLI) is the most progressed stage of peripheral arterial occlusive disease (PAOD), drastically reducing blood flow to the lower limbs and causing claudication and even tissue loss. Patient prognosis can be improved, and downstream tissue salvaged through the enlargement of collateral arterioles that form a natural bypass around atherosclerotic occlusions in major arteries. The ability of collaterals to enlarge through arteriogenesis varies greatly among individuals, with accompanying cardiovascular risk factors such as hypertension, diabetes, and obesity impairing collateral arteriogenesis, due to their disruption of endothelial dysfunction. Despite promising results in rodent models, a variety of cell-based therapies have failed to improve patient outcome during clinical testing. Currently, there is no reliable clinical therapy to enhance collateral arteriogenesis.

There are approximately 20 million patients in the United States with Peripheral Arterial Disease (PAD), and approximately 2 million patients with Critical Limb Ischemia (CLI), the most severe form of PAD. At the time of clinical presentation, 50% of patients with CLI are candidates for surgical (i.e. bypass grafting) or endovascular (i.e. angioplasty) revascularization, while 25% undergo amputation, and the remaining 25% are managed pharmacologically. In the treated population, at 1 year, CLI is resolved in 25% of patients, while 25% die, 30% undergo amputation, and 20% remain symptomatic.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION

Figure 1:
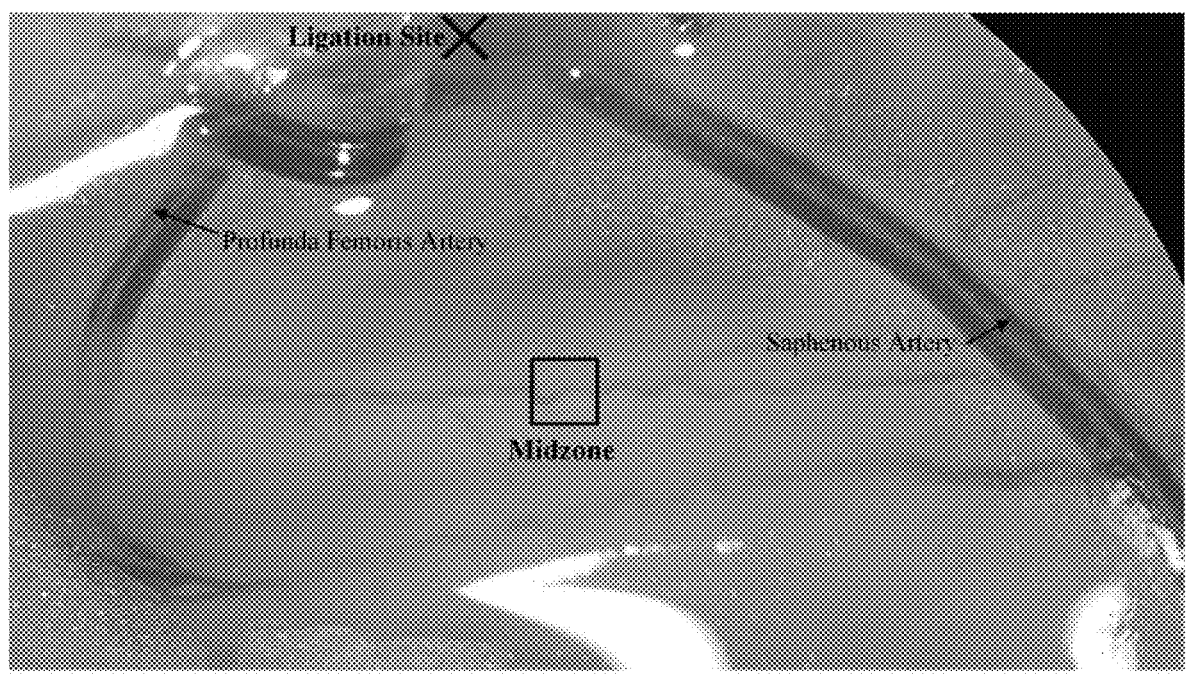
FIG. 1 is a photograph showing the medial hindlimb of the mouse.

Peripheral artery disease (PAD) affects 8-12% of the adult US population [65], with up to 15-20 million people affected in the United States. PAD can lead to critical limb ischemia (CLI), the most severe manifestation of the disease, with approximately 2 million CLI patients in the United States [17]. The prognosis for patients with CLI is poor, with 25% undergoing amputation as the primary treatment and only 50% treated by surgical or endovascular revascularization [40]. After 1 year, CLI is resolved in only 25% of patient, while 20% remain symptomatic, 30% undergo amputation, and 25% die [40]. The poor prognosis for these patients indicates that new treatments methods are needed.

A possible treatment for patients with PAD is to enhance the growth of natural bypass collateral arterioles. Collaterals are pre-existing arterial-arterial anastomoses that can serve as natural bypasses around arterial occlusions. In PAD patients, a well-developed collateral circulation improves performance on the 6-minute walk test and slows performance decline over time [36, 37]. Note that although on occasion when discussing collaterals the term collateral arteries is used. However, more properly these are referred to as collaterals, since arteries per se are outside organs and tissues. Not limited to the leg, collaterals in the coronary circulation improve myocardial viability, reduce the risk for a repeat cardiac event, and a lower hospital mortality rate following heart attack or revascularization [39, 45, 52]. Unfortunately, there are no approved cell (or gene)-based therapies to treat PAD and critical limb ischemia.

The increased shear stress commensurate with the increased blood flow through the collateral activates the endothelium in a classic inflammatory response, including monocyte recruitment from the circulation. Following migration and differentiation from monocytes, macrophages secrete proteases to degrade the extracellular matrix, and mitogens to promote endothelial and smooth muscle proliferation to enable vessel enlargement (i.e. arteriogenesis). Once the collateral has enlarged sufficiently to normalize shear stress across the endothelium (i.e. a larger diameter decreases the velocity of a given flow and therefore decreases the shear), endothelial cells 'inactivate' and the inflammatory response resolves [20]. Therefore, it seems as if it would be straightforward to enhance collateral arteriogenesis by delivering cells that participate in the process or secrete factors involved in controlling the process. Indeed, in most animal studies, cell based therapies are effective at ameliorating ischemia [25, 31, 34]. Unfortunately, numerous attempts to stimulate collateral arteriogenesis with cell therapy in human clinical trials have failed [44, 50, 64]. There are likely many possible explanations for the disparity between the effectiveness of cell based therapies in animal models as compared to human patients [31, 34, 35] but a likely major contributor is the absence of co-morbidities in most animal models. Co-morbidities common to patients with PAD, such as hypercholesterolemia, diabetes, and obesity, induce endothelial dysfunction and impair arteriogenesis responses in laboratory animals [16, 60-62] and patients [56].

Possibly due to the added expense and increased variability of animal models with comorbidities, there are relatively few studies evaluating cell therapy candidates in these animals. However, in the studies that are available, cell therapy is expected to range from as effective to less effective in animals with comorbidities, as compared to animals without. While collaterals are the primary site of blood flow resistance to the ischemic tissue [59] and therefore the most significant anatomical structure to assess following a cell therapy, hindpaw perfusion, angiogenesis, hindpaw necrosis all correlate with arteriogenesis [19, 72]. Specifically, bone marrow mononuclear cells lead to less perfusion recovery and less angiogenesis in obese and diabetic (insulin resistant) rats, as compared to lean rate [33]. Endothelial progenitor cells exhibit no different in arteriogenesis (angiographic score) and angiogenesis in hyperglycemic rabbits [73]. Similarly, in hyperglycemia rats, blood flow recovery in response to bone marrow cells is not different than in normoglycemic rats [23]. This suggests that in rats and rabbits, the combination of multiple comorbidities is necessary to impair the efficacy of revascularizing cell therapies. In mice, the presence of hyperglycemia alone negates the reduction of hindpaw necrosis by bone marrow mononuclear cells [58]. It appears that the addition of genetically-induced hypercholesterolemia to hyperglycemia does not further impair perfusion recovery or angiogenesis, though direct comparisons were not made [6]. However, in obese and diabetic (insulin resistant) mice, endothelial progenitor cells are no better than phosphate buffered saline (PBS) at promoting perfusion recovery or reducing hindpaw necrosis unless pre-treated with an angiogenic factor [71]. Interestingly, in a similar obese and diabetic (insulin resistant) mouse model, a stem cell mobilizing agent mildly improves perfusion recovery and angiogenesis (beyond PBS), but does not enhance arteriogenesis [13].

As shown in the examples below, the inventors implemented an animal model that correlates with human metabolic disorder including elevated body weight and adiposity, mild hypertension and insulin resistance, using mice with diet-induced obesity (DIO). The methods for treatment used satellite cell-derived myoblasts and administered the myoblasts to the obese animals. The treatment was also administered to animals having natural genetic alterations that result in the phenotype of impaired arteriogenesis. Surprisingly, it was found that administration of the myoblasts increased maximal collateral diameter in the obese and genetically-deficient animals but not in lean (non-obese) animals. In an embodiment the maximum diameter of the at least one collateral is increased by up to 5%, by at least 5%, 6%, 7%, 8%, 9%, 10%, 15%, 20%, 25%, 30%, 35%, 40%, 50%, 55%, 60%, 65%, 70%, 75%, 80%, 85%, 90%, 95% or more or amounts in between. This results in increased blood flow in the collateral. In an embodiment the blood flow is increased by at least 10%, 20%, 30%, 40%, 50%, 60%, 70%, 80%, 90%, 100%, 110%, 120%, 130%, 140%, 150%, 160%, 170%, 180%, 190%, 200% or more or amounts in between.

Unlike bone marrow mononuclear cells or endothelial progenitor cells, skeletal muscle myofiber-derived myoblasts require no pre-treatment with pro-regenerative factors to enable their efficacy [13, 71]. Additionally, unlike bone marrow mononuclear cells or endothelial progenitor cells, myoblasts were found to be selectively effective in contexts in which arteriogenesis is impaired by the presence of comorbidities or the absence of genetic loci involved in promoting a robust arteriogenesis response. The divergent response of myoblasts with bone marrow mononuclear cells and endothelial progenitor cells is of particular interest because of the failure of the latter cell types in randomized clinical trials. The success of myoblasts in environments in which the other cell types are less effective or ineffective reflects a greater clinical utility of myoblasts.

Satellite cells are stem cells that lie adjacent to a skeletal muscle fiber. They are located between the sarcolemma and basal lamina of the muscle fiber. The cells express the proteins M-cadherin, c-Met, Pax7, the adhesion molecule N-CAM and myogenic regulatory factor Myf5.72. Satellite cells are surrounded by M-caherin. Myoblasts are produced by (derived from) the satellite cells and can mature into myocytes before fusing to form myotubes, which are capable of repairing injured existing muscle fiber or regenerating entire muscle fibers [9, 57, 70] Satellite cells are precursors to myoblasts and divide to provide myonuclei to growing and repairing myofibers. Myoblasts are also the embryonic precursors of myocytes. For the first time, there is here shown administration of these cells that can treat peripheral artery disease by enhancing arteriogenesis in animals and so reduce ischemia resulting from PAD. In an embodiment the animals are overweight/obese. In another embodiment the animals have a natural genetic variation that results in the phenotype of impaired arteriogenesis.

An animal has adiposity or is obese which the amount of fat in the animal body exceeds that of normal distribution of animals. Such adiposity causes increased adverse impact on the health of the animal compared to an animal not having such increased fat. The adverse impact can extend to hypertension, hypercholesteremia, increase cardiovascular risks and produce an increased ischemia as a result of arterial occlusions. In one embodiment, the animal has body fat content that causes one or more of the conditions described above or which have been correlated to obesity.

To determine if an animal is obese, for example, one can evaluate average weight over time and identify a statistically significant increase. Another example is to generate a normal distribution of weights of a population of animals and then estimate obesity with the distribution. Examination of body conditions and scoring such conditions may be used. For example, obesity in one instance occurs when body weight that is 20% or more in excess of ideal weight:height ratio according to actuarial tables. weight:height ratio according to actuarial tables.

Still another example uses a body condition score, such as that used in dairy cattle to estimate obesity in the strain or population. This is compared to standards by which to assess the condition of animals [29].

The Obesity Medicine Association refers to obesity as an increase in body fat promoting adipose tissue dysfunction and abnormal fat mass physical forces, resulting in adverse metabolic, biomechanical, and psychosocial health consequences [68]

That ideal weight will take into account, in the instance of humans, the person's height, age, sex, and build. Obesity in one instance is described by the National Institutes of Health (the NIH) as a BMI of 30 and above. BMI uses a simple calculation based on the ratio of someone's height and weight (BMI=kg/m2). For adult men and women, a BMI between 18.5 and 24.9 is considered healthy. Overweight is defined as a BMI between 25.0 and 29.9; and a BMI of 30 or higher is considered obese. In children and adolescents age 2 to 20 years old, a BMI in the 85th to 94th percentiles for age and gender is considered overweight; a BMI in the 95th percentile or higher is considered obese. For children aged between 5-19 years overweight is BMI-for-age greater than 1 standard deviation above the WHO Growth Reference median and obesity is greater than 2 standard deviations above the WHO Growth Reference median [2]

A still further example of measuring obesity is waist size. Guidelines generally define abdominal obesity in women as a waist size 35 inches or higher, and in men as a waist size of 40 inches or higher. Still other examples of measuring obesity include methods using specialized equipment, such as magnetic resonance imaging or dual energy X-ray absorptiometry machines; while these machines can measure body fat very accurately, they are typically only used for this purpose in research settings. Peterson et al. have further developed ideal body weight formulas, for example, using BMI. One such example is to determine body weight in pounds, the desired BMI is multiplied by 5 and then add BMI/5 lb for each inch >5 ft in height [47].

Animals having genetically induced impaired arteriogenesis demonstrate such a phenotype as a result of a genetic modification that can be caused by any number of variations. The genetic modification may be the result in the animal of a deletion of all or part of the sequence of a gene or amino acid sequence produced; an addition of sequences to all or part of the gene or amino acid sequence produced; or change in all or part of the sequences of the gene or amino acid sequence produced that results in the change in phenotype. One of skill in the art appreciates there are a variety of such genetic modifications that produce the phenotype. In one example Wang et al. identified a major quantitative trait locus on chromosome 7, Canq1, responsible for 37% of the heritable variation in collateral extend between C57BL/6 and BALB/c mice [67]. Another group identified the limb salvage-associated quantitative trait locus 1 on mouse chromosome 7 as the first genetic modifier of perfusion recovery and tissue necrosis phenotypes. Furthermore, a number of genes within LSq-1, such as ADAM12, IL-21Ra, and BAG3 were identified as genetic modifiers of peripheral artery disease severity [41]. By way of example, see ADAM metallopeptidase domain 12 [Homo sapiens (human)] Gene ID No 8038, Ensembl:ENSG00000148848 MIM:602714 Chromosome 10: 126,012,381-126,388,455 reverse strand, GRCh38:CM000672.2; l21r.2 interleukin 21 receptor, tandem duplicate 2 [Danio rerio (zebrafish)] Gene ID No 100134975, Ensembl:ENSDARG00000078649; and BAG3 BAG cochaperone 3 [Homo sapiens (human)] Gene I 9531, Ensembl:ENSG00000151929 MIM:603883.

The myoblasts cells may be introduced or administered in any suitable manner, such that the myoblast is sufficiently close to the collateral so as to allow signaling or cell to cell communication to occur when paracrine factors released from the myoblast cells or myoblast cells may contact one or more collateral arterioles. Paracrine factors include, but are not limited to peptides, proteins, and extracellular vesicles containing either or both protein/peptide or nucleic acid cargo, which are synthesized by one cell and can diffuse to induce and changes in neighboring cells, an event called paracrine interaction and the diffusible factors are called paracrine factors.

Any method of administration that causes the myoblast cells to come into contact with the at least one collateral or close proximity allowing paracrine factors released from the myoblasts cells to induce paracrine interaction with the collaterals may be used. Such paracrine factors are known and by way of example, many of these paracrine factors can be grouped into four major families on the basis of their structures. These families are the fibroblast growth factor (FGF) family, the Hedgehog family, the Wingless (Wnt) family, and the TGF-β superfamily [55]. Over a dozen distinct FGF genes are known in vertebrates. The Hedgehog proteins constitute a family of paracrine factors that are often used by the embryo to induce particular cell types and to create boundaries between tissues. The Wnts constitute a family of cysteine-rich glycoproteins. There are at least 15 members of this family in vertebrates. There are over 30 structurally related members of the TGF-b superfamily, and they regulate interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell.

By way of example without limitation such methods include by transplantation in an area sufficiently adjacent to the collaterals to provide for paracrine interaction or contact with collaterals, immersion in a composition or substance containing the cells, parenterally, by injection subcutaneously or intramuscularly, or into an organ or cavity of the animal. In a further embodiment the cells are administered such that they come into contact with muscle cells comprising at least one collateral. The cells and a composition comprising the cells can be administered by any means which includes, but is not limited to, syringes, nebulizers, misters, needleless injection devices, or microprojectile bombardment gene guns (Biolistic bombardment), via a liposome delivery system, naked delivery system, electroporation, viruses, vectors, viral vectors, or an ingestible delivery system wherein the cells are consumed, for example, in food or water or in any other suitable manner. The preparations are administered in a manner compatible with the dosage formulation, and in such amount as will be therapeutically effective in increasing diameter and/or blood flood and/or reduce ischemia.

The quantity to be administered depends on the subject to be treated. In one embodiment, a straightforward and quick method can be administering the cells and then measure change in diameter, blood flow or ischemia. There are various options available to the skilled person. The number of cells introduced can take into consideration factors such as sex, age, weight, the types of disease or disorder, stage of the disorder, the percentage of the desired cells in the cell population (e.g., purity of cell population), and the cell number needed to produce the desired result.

Generally, for administering the cells for therapeutic purposes, the cells are given at a therapeutically effective or pharmacologically effective dose. By "therapeutically effective dose" or "pharmacologically effective amount" or "pharmacologically effective dose" is an amount sufficient to produce the desired physiological effect or amount capable of achieving the desired result, particularly for treating the condition or disease, including reducing or eliminating one or more symptoms or manifestations of the condition or disease. Pharmacologically effective doses will also apply to therapeutic compounds used in combination with the cells.

Suitable regimes for initial administration and additional administrations are also variable but may include an initial administration followed by subsequent administrations. In some embodiments, the composition comprising the myoblasts is administered to the subject once. In other instances, the composition is administered at one time point, and administered again at a second time point. In yet other instances, the compound is administered to the subject repeatedly (e.g., once or twice daily) as intermittent doses over a short period of time (e.g., 2 days, 3 days, 4 days, 5 days, 6 days, a week, 2 weeks, 3 weeks, 4 weeks, a month, or more). In some cases, the time between compound administrations is about 1 day, 2 days, 3 days, 4 days, 5 days, 6 days, a week, 2 weeks, 3 weeks, 4 weeks, a month, or more. In other embodiments, the composition is administered continuously or chronically in accordance with a chronic regimen over a desired period of time. For instance, the compound can be administered such that the amount or level of the compound is substantially constant over a selected time period.

As is evident to one of skill in the art, a composition comprising the myoblast cells can include any other useful components. Examples include adjuvants, carriers, excipients, diluents or the like. A pharmaceutically acceptable carrier may be used for administration of the cells to the subject. These will typically comprise, for example, buffered saline (e.g., phosphate buffered saline) or unsupplemented basal cell culture medium, or medium as known in the art. In certain aspects, pharmaceutically acceptable carriers are determined in part by the particular composition being administered, as well as by the particular method used to administer the composition. Accordingly, there is a wide variety of suitable formulations of pharmaceutical compositions [1]. As used herein, "pharmaceutically acceptable carrier" comprises any of standard pharmaceutically accepted carriers known to those of ordinary skill in the art in formulating pharmaceutical compositions. Thus, the cells can be introduced by themselves, or with compositions being present as pharmaceutically acceptable salts, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients. Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as wetting agents; emulsifying agents; or suspending agents.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathioneas appropriate.

As used herein, the term "unit dosage form" refers to physically discrete units suitable as unitary dosages for humans and other animals or mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the therapeutic composition.

Methods for preparing such dosage forms are known to those skilled in the art [1]. The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art [1].

Other embodiments of the compositions described herein are kits comprising a population of myoblast cells and optionally other pharmaceutically acceptable compounds. The kit typically contains containers which may be formed from a variety of materials such as glass or plastic, and can include for example, bottles, vials, syringes, and test tubes. A label typically accompanies the kit, and includes any writing or recorded material, which may be electronic or computer readable form providing instructions or other information for use of the kit contents.

The following is provided by way of exemplification and is not intended to limit the scope of the invention. References cited herein are incorporated herein by reference.

EXAMPLES

Given that bone-marrow mononuclear cells have failed to improve patient outcomes in large, randomized clinical trials [44], it appears that the combination of comorbidities in animal models is the most likely to predict clinical outcome. Therefore, we completed our studies in mice with diet-induced obesity. These mice, fed a 60% fat diet from 4-weeks-of age and studied at 4-months-of-age, develop most elements of human metabolic disorder, including elevated body weight and adiposity, mild hypertension, and insulin resistance [14]—all common comorbidities for patients with PAD [40].

Having selected an animal model that is likely predictive of human clinical responses, our next task was to select a candidate cell therapy. To date no successful alternative has been developed. Bone marrow derived cells have failed in clinical trials [44]. We developed a hypothesis to utilize a non-bone marrow cell, and instead use a skeletal muscle-derived cell. The local niche is critical in maintaining stem/progenitor cell properties and paracrine signaling [18, 28]. For example, resident mesenchymal stem cells (MSC) are more effective at differentiating into skeletal muscle [38] and cartilage [15] than bone-marrow derived MSCs. Our hypothesis continued that due to niche signaling muscle-derived cells may more effectively communicate with the cells regulating arteriogenesis in skeletal muscle arterioles. Within the myo-vascular niche, we speculated that the most promising candidate would be a cell that impacts the cells involved in arteriogenesis. Using this rationale, we selected myoblasts derived from satellite cells. Satellite cells promote monocyte recruitment [5, 53] and alter macrophage polarization [24, 43], and promote angiogenesis [10, 48, 49]. This indicates that satellite cells and/or their myogenic progeny communicate with macrophages and endothelial cells—the two most important cells in regulating arteriogenesis [12, 21]. The present hypothesis is not obvious to those trained in art when understanding the primary literature is to muscle repair/regeneration and the biology of vascular growth/remodeling. For example, myoblasts have only been evaluated clinically for their myogenic properties, to promote muscle repair in muscular dystrophies [42], myocardial repair following infarction [11], and urinary incontinence [63]. When myoblasts have been explored for stimulating angiogenesis, they are often genetically modified to express angiogenic factors [4, 32, 51], reducing the contribution of the myoblast to that of a gene vector. In the present methods it has been surprisingly discovered that it is not necessary to so modify myoblast nor to chemically stimulate the myoblast to produce additional angiogenic factors to achieve the results shown. An embodiment provides administration of the myoblasts wherein the maximum collateral diameter is increased and wherein the myoblast is not altered genetically nor chemically to produce arteriogenic factor. Therefore, it is clear from the primary literature that to those skilled in art, myoblasts are not a cell therapy candidate for enhancing arteriogenesis.

Therefore, we tested the hypothesis that myoblasts derived from satellite cells would enhance arteriogenesis in mice with diet-induced obesity.

Results

Figures 2A, 2B:
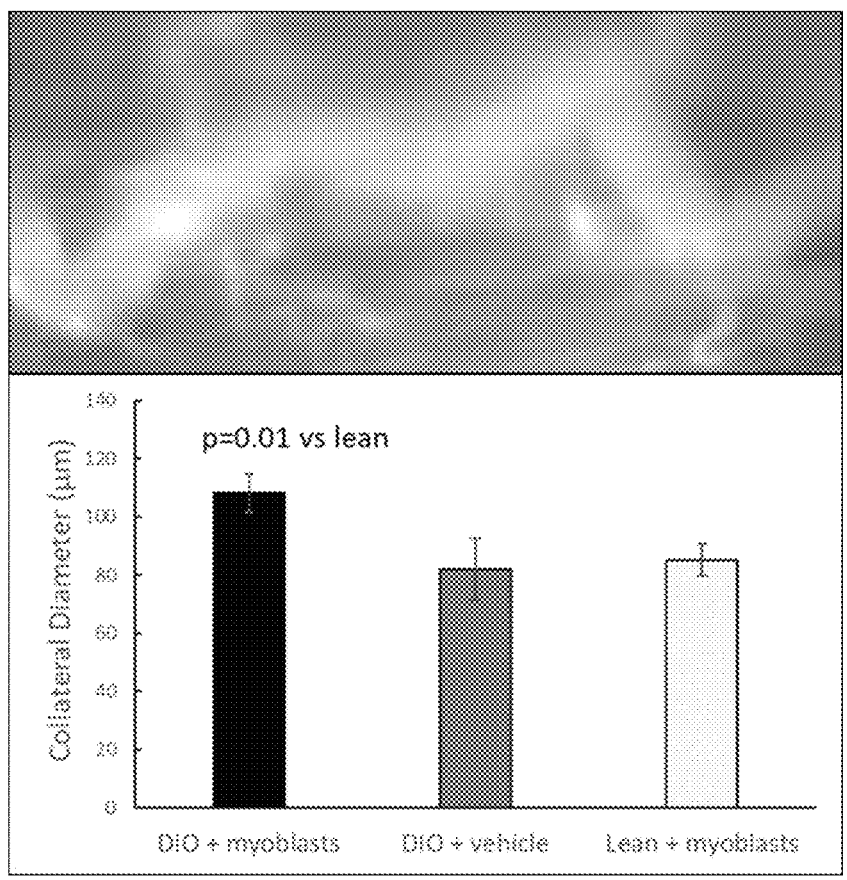
FIG. 2A is a photograph showing enhanced collateral arteriogenesis after myoblast transplantation in mice and FIG. 2B is a graph summarizing collateral diameter change as a result of transplantation with the identified compositions.

FIG. 1 shows the Profunda Femoris Artery and Saphenous Artery are connected by a natural bypass collateral in the gracilis anterior muscle. Normally, blood is supplied to the proximal half of gracilis anterior muscle by arteriolar branches from the profunda femoris artery, while blood is supplied to the distal half of the gracilis anterior muscle by arteriolar branches from the saphenous artery. Upon ligation, blood flows from the profunda femoris artery, through the collateral, and then into the saphenous artery. The elevated shear stress in the collateral induces arteriogenesis. We assessed arteriogenesis at day-7 following artery ligation, because enlargement is complete by this time [22]. As shown in FIG. 2, myoblast transplantation enhances arteriogenesis in mice with diet-induced obesity (DIO). FIG. 2 demonstrates enhanced collateral arteriogenesis following myoblast transplantation in mice with diet-induced obesity (DIO). Arteriogenesis was assessed by intravital microscopy in the primary hindlimb collateral, i.e. the collateral with the lowest vascular resistance, which is located in the gracilis anterior muscle. These measurements were performed in C57Bl/6 male mice fed a 60% fat diet from 6-weeks-of-age to ~4 months (myoblasts, n=6; gelatin vehicle, n=5) or in lean C57Bl/6 male mice of the same age (myoblasts, n=6). Arteriogenesis was quantified by electrically stimulating the collateral-containing skeletal muscle to induce a maximal vasodilation response; arteriogenesis is most reliably assessed my measuring maximum diameter. Of specific importance to this application, maximum collateral diameter was greater in mice with DIO transplanted with myoblasts than in lean mice transplanted with myoblasts. This unique observation is in contrast to a majority of previously reported studies of cell therapy in laboratory animals with comorbidities, which typically exhibit a reduced or absent response to bone marrow derived cells or endothelial progenitor cells.

Figures 3A, 3B:
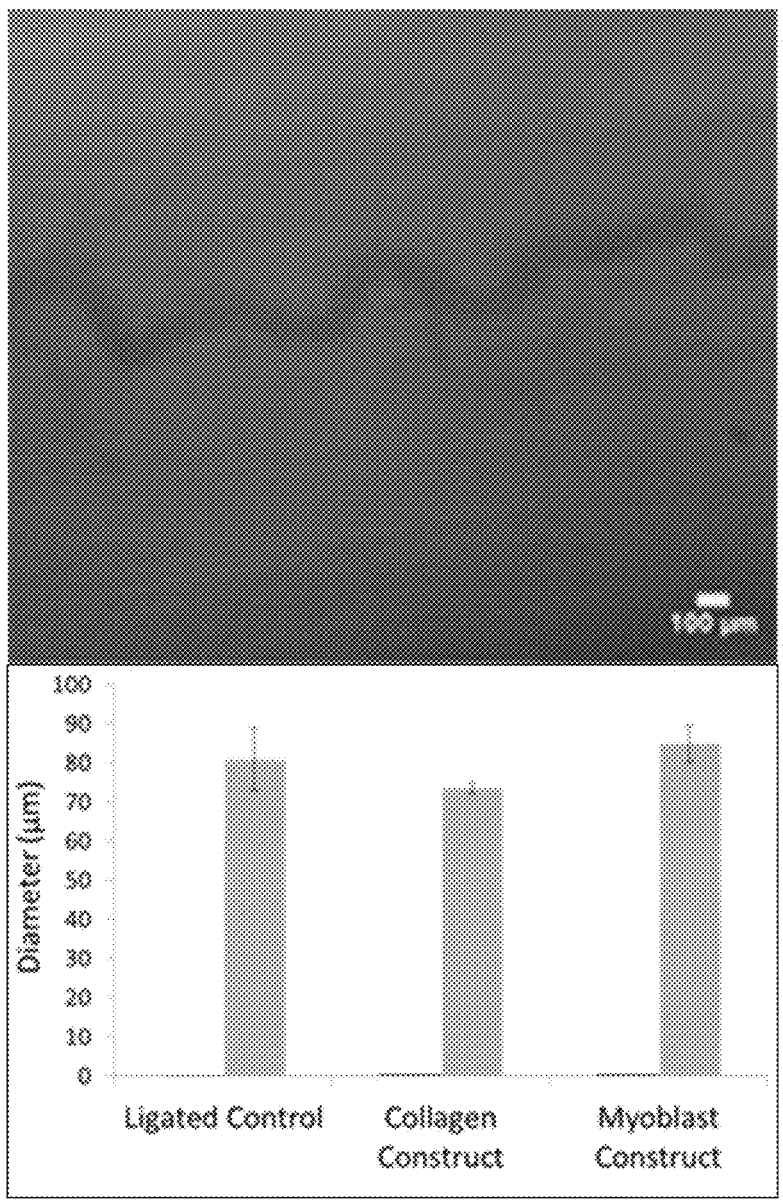
FIG. 3A is a photograph showing lack of collateral arteriogenesis in lean mice following transplantation.
FIG. 3B is a graph showing collateral diameter change as a result of transplantation with the identified compositions.

The 32% greater collateral diameter in the mice with DIO that received myoblast transplantation, as compared to the lean mice that received myoblast transplantation, would translate to a 200% increase in blood flow, owing to the $4^{th}$ power relationship between vessel diameter and resistance/conductance, as defined in the Poiseuille-Hagan Equation, which states that blood flow=conductance×pressure gradient, and conductance=$(\pi \cdot D^4)/(128 \cdot \eta \cdot \iota)$ [30]. This increase in blood flow would increase downstream tissue oxygenation, which in turn decreases tissue injury, inflammation, and necrosis, and simultaneously improves tissue function. Interestingly, despite their arteriogenic effect on collaterals in mice with DIO, myoblasts are unable to enhance arteriogenesis in lean mice (FIG. 3). FIG. 3 demonstrates a lack of enhancement of collateral arteriogenesis following myoblast transplantation in lean (non-obese) mice. Arteriogenesis was assessed by intravital microscopy in the primary hindlimb collateral. These measurements were performed in C57Bl/6 male mice fed a standard diet, and aged 2-3 months (myoblasts, n=4; collagen vehicle, n=4; ligation only n=3).

Figure 4:
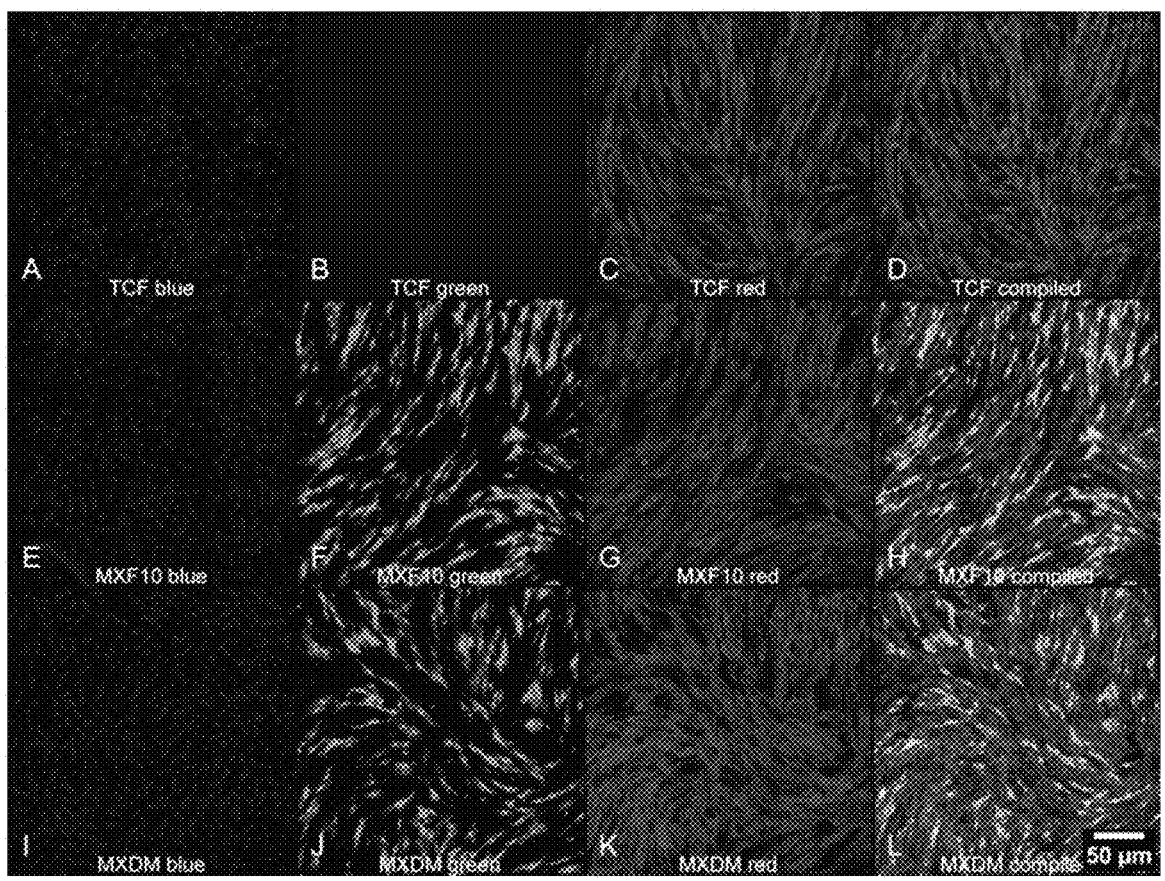
FIG. 4 is a photograph showing myogenic identity of cells used for transplantation.

As shown in FIG. 4, the cells we transplanted, which were isolated from individual myofibers, are a pure population of myogenic cells. The antibody used to label M-cadherin does not react with fibroblasts, and there appear to be no non-reactive myogenic cells. FIG. 4 demonstrates the myogenic identity of the cell-type used for transplantation, and the specificity of the antibody used for myoblast identification, as it does not react with fibroblasts. The nuclei of all cells were stained with NucBlue (blue), fibroblasts were genetically modified to express Green Fluorescent Protein (GFP), and myoblasts cells were labeled with a primary antibody reactive to M-cadherin and a secondary antibody conjugated to Alexa Fluor 594 (i.e. red). Myoblasts in culture (TCF, A-D), myoblasts co-cultured with fibroblasts in myoblast media (MXF10, E-H), and myoblasts co-cultured with fibroblasts in fibroblast media (MXDM, I-L) demonstrate that only myoblasts are labeled by the antibody that reacts to M-cadherin.

As discussed above, arteriogenesis can be impaired by comorbidities that induce endothelial dysfunction, but also by genetic mechanisms, such as in mice from the BALB/c strain, which have reduced collateral number and arteriogenesis responses [66, 67]. Specifically, gene variants in quantitative trait loci on chromosome 7 and chromosome 11 have a significant impact on the number of native collaterals and their remodeling, respectively. The genetic variants can, for example, be point mutations, missense in which a nucleotide produces a different amino acid from normal phenotype amino acids, a codon change that has similar properties but produces abnormal phenotype, duplications, deletions and insertions just to name a few. In an embodiment a sample is obtained from the animal and assayed to determine if the genetic modification that produces the impaired arteriogenesis phenotype is present. Many methods are available to such an assay. The sample can be any convenient sample such as animal tissue, fluid or cell which are expected to have the nucleic acid or the amino acid produced, whether blood, skin, organ tissue, body fluids or the like. A vast methodology is available to one of skill in the art in detecting the presence of a genetic modification. By way of example without limitation, one can detect the presence of absence of a nucleotide sequence, the presence or absence of a protein that has been modified, determine if too much or too little protein is produced, or if there is incorrect localization of the protein associated with a genetic modification. Primers and probes can be utilized to detect the presence or absence of particular sequences. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed [26, 27, 54]. Moreover, current techniques which employ the PCR reaction permit the synthesis of genes as large as 1.8 kilobases in length [3, 7]. Known methods of PCR include, but are not limited to, methods using paired primers, nested primers, degenerate primers, gene-specific primers, vector-specific primers, partially-mismatched primers, and the like. All or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $32^P$, or any other detectable marker. Thus, for example, probes for hybridization can be made by labeling synthetic oligonucleotides based on the DNA sequences. Methods for preparation of probes for hybridization and for construction of cDNA and genomic libraries are generally known in the art and are disclosed [54].

Figure 5:
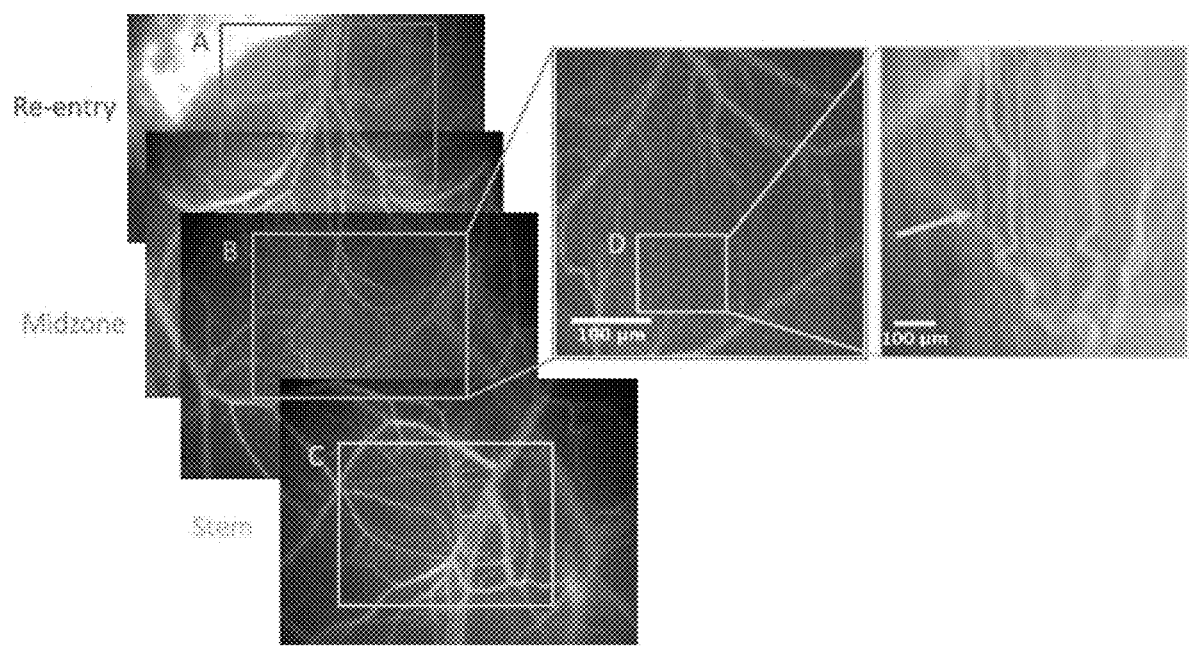
FIG. 5 are photographs showing a portion of the spinotrapezius muscle in a BALB/c mouse, in which capillaries form a natural bypass connection between terminal arterioles of the anterior arteriolar tree labeled (A) and the posterior arteriolar tree (B). Upon ligation of the artery that feeds the anterior arteriolar tree, the collateral capillaries (C) between the anterior and posterior arteriolar trees will arterialize and become functional bypass collaterals (D).
Figures 6A, 6B:
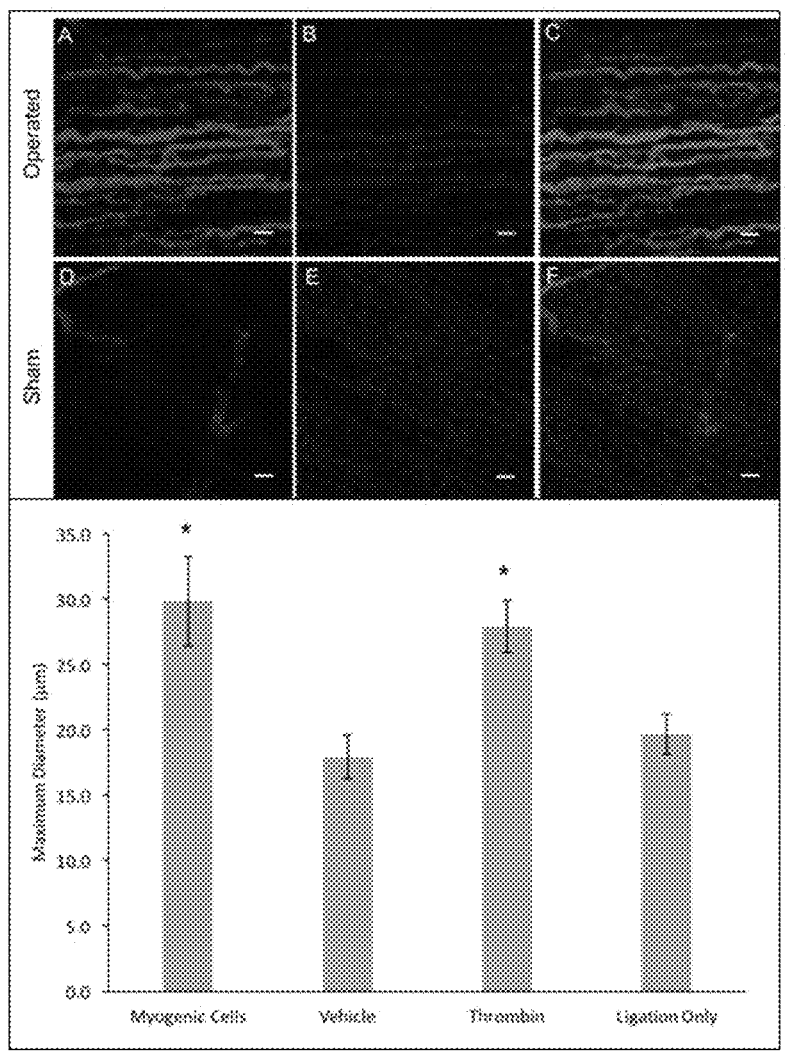
FIG. 6A are photographs showing enhanced collateral capillary arteriogenesis following myoblast transplantation in BALB/c mice and FIG. 6B is a graph showing maximum diameter of collaterals when treated as indicated.

The reduced collateral number due to gene variants gives rise to microvascular beds that lack collateral arterioles, but do have collateral capillary anastomoses (FIG. 5). Consistent with their potency in C57Bl/6 mice with DIO, but not lean C57Bl/6 mice, myoblast transplantation enhances collateral capillary arteriogenesis in BALB/c mice (FIG. 6). FIG. 6 demonstrates enhanced collateral capillary arteriogenesis following myoblast transplantation in BALB/c mice. Arteriogenesis was assessed by immunofluorescence and confocal microscopy of collateral capillaries in the spinotrapezius muscle. These measurements were performed in BALB/c male mice aged 2-4 months (myoblasts, n=4; gelatin vehicle, n=4; thrombin positive control, n=3; ligation only, n=3.

Arteriogenesis in these experiments was assessed by maximally vasodilation immediately followed by fixation with paraformaldehyde.

Experimental Procedures

Myoblast Isolation

Mice (3-12 week old) were euthanized by cervical dislocation while anesthetized with 1-3% isoflurane gas with a flow rate of 0.8-1 $l \cdot min^{-1}$. In a supine position, all limbs were pinned with syringes and the mice were disinfected with 70% isopropanol, and the skin was removed from the knee to the inferior aspect of the hindpaw. The tibialis anterior (TA) was carefully resected to expose the extensor digitorum longus (EDL) on both limbs. The distal tendon of the EDL was cut and the muscle was gently separated from the underlying connective tissue. The muscle was then removed via the proximal tendon from both limbs.

Excised muscles were placed in a digestion solution (2 $mg \cdot mL^{-1}$ type 2 collagenase [Worthington CLS-2], 1% Penicillin-Streptomycin [Omega PS-20] in HAMS F10 [Fisher SH3002501]) and incubated in a water bath at 37° C. for 45-70 minutes. Every ten minutes, the solution was inverted to mix. Myofibers were then mechanically separated from the EDL by trituration using custom, 4 mm inner diameter, beveled, glass pipettes lubricated with horse serum (HS) in a tissue culture dish filled with wash media (HAMS F10 supplemented with 10% FBS [Fisher SH3091003], 1% Pen-Strep) maintained at 37° C. Isolated myofibers were washed 3 times in wash media before placement in a flask coated over night with ECM Gel (Sigma E1270-1ML). To prepare culture media, wash media was supplemented with 2 $ng \cdot mL^{-1}$ bFGF [Fisher CB40060] and 2 $ng \cdot mL^{-1}$ p38 inhibitor [SB 203580, Fisher 120210]). Myofibers were incubated in culture media at 37° C. with 5% $CO_2$.

Myoblast Subculture

Myofiber cultures were assessed daily using a phase-contrast microscope. Typically, punitive satellite cells (myofiber associated skeletal muscle stem cells) began migrating from fibers onto the flask after two days. Cultures were passaged when the majority of myofibers exhibited hypercontraction or the confluency reached 80%. For passaging, the flask was titurated with a dissociation buffer (Fisher-Gibco 13151014) until the majority of the cells were suspended. The media was centrifuged at 0.3 rcf for 10 min and the pellet was resuspended in culture media. The cells were seeded onto a new coated flask at no less than 20% confluency, and were again passaged at 80% confluency. Once the cell population reached approximately 4 million, they were either used or cryopreserved in 1 million-cell aliquots in 80% FBS (Fisher SH3091003) and 20% DMSO (SIGMA D2650).

Myoblast Transplantation (FIGS. 2 and 6)

A 10% Gelatin (Sigma G1890-100G) vehicle was cross-linked with 1-Ethyl-3-(3-dimethylaminopropyl) carbodiimide (Fisher PI22981) overnight. Myoblasts were released from culture flasks and sodded onto the surface of a gelatin vehicle at a density of $2.5 \times 10^5$ cells $cm^{-2}$ in well plates and incubated for 6 or 12 hours before transplantation. During ligation surgery, the gracilis anterior or spinotrapezius were undermined using blunt dissection to create a 'pocket' as close as possible in the middle of the collateral(s). A 1.5 mm gelatin disc (with or without myoblasts) was prepared with a biopsy punch (INTEGRA YORK PA INC. 33-31A-P/25), and gently placed in the 'pocket', with the cell-containing side of the gelatin in contact with the deep side of the skeletal muscle. With a 1.5 mm biopsy punch having a 1.77 $mm^2$ surface area, approximately $4.4 \times 10^3$ cells transplanted.

Myoblast Transplantation—FIG. 3

Myoblasts were released from culture flasks and centrifuged at 300 g for 10 minutes before removing the supernatant. On ice, the cell pellet was resuspended in a solution of sterile $H_2O$, 4× concentrated DMEM, and rat tail collagen (6 $mg \cdot mL^{-1}$) to yield $2.5 \times 10^5$ cells per 50 µl. The solution was pH corrected with 0.1M NaOH and transferred in 50 µL volumes to wells of a flat bottom 96-well plate. The construct was allowed to polymerize for a minimum of 1 hour at 37° C. with 5% $CO_2$. An identical protocol was followed minus the resuspension of myoblasts to create vehicle-only controls. During ligation surgery, the gracilis anterior was undermined using blunt dissection to create a 'pocket' as close as possible in the middle of the collateral(s). Polymerized collagen vehicles, with or without cells, were gently removed from the well plate and placed deep to the muscle in the 'pocket'.

Myoblast Immunofluorescence

Myoblasts were released, sodded into an 8-well chamber slide, and incubated for 24 hours. Fibroblasts were released, sodded into the same 8-well chamber slides, and incubated for 6 hours. Cells were then washed twice with phosphate buffered saline (PBS) before fixing with 4% paraformaldehyde for 20 min at room temp. After fixation, cells were washed twice with PBS before the application of the M-cadherin primary antibody solution (1:200 in PBS containing 5% bovine serum albumin [BSA]) at room temp for 2 hours or overnight at 4° C. After primary antibody application, cells were washed twice with PBS, before applying the AlexaFluor 594-conjugated secondary antibody solution (1:300 in PBS) with 5% BSA at room temperature for 2 hours. Fifteen minutes before removing the secondary antibody solution, 1 drop of NucBlue was added to each well to stain nuclei.

Femoral Artery Ligation Surgery

Mice were anesthetized in an induction chamber with 3% isoflurane gas with an oxygen flow rate of 0.8-1.1 $l \cdot min^{-1}$. Using a nose cone, mice were maintained in an appropriate plane of anesthesia with 1-2% isoflurane gas at the same oxygen flow rate for the remainder of the procedure. Mice were weighed, transferred to a preparatory station, and buprenorphine analgesic was administered (0.075 $mg \cdot kg^{-1}$, subcutaneously). The surgical site was prepared by removing the hair from the medial surface of both hindlimbs and disinfecting the skin with chlorohexidine diacetate. Mice were then transferred to the surgical stage and a rectal thermistor was used to maintain core body temperature at 35° C.; ophthalmic ointment was placed over the cornea to prevent desiccation. Through an incision in the medial aspect of the hindlimb, the femoral nerve and vein were gently separated from the neurovascular bundle by blunt dissection. The femoral artery was ligated with a strand of 6-0 silk suture, downstream of the profunda femoris/epigastric artery branch(es) and upstream of the popliteal artery branch. After ligation, a 'pocket' was created for cell or vehicle-only transplantation, as described above. The skin incision was closed with 7-0 polypropylene suture, and a sham surgery was performed on the contralateral leg. The sham surgery included a skin incision and blunt dissection around the ligation site, but no separation of the neurovascular bundle. Post-operative buprenorphine (0.075 mg·kg$^{-1}$) was administered subcutaneously and animals were allowed to recover until ambulatory.

Lateral Spinotrapezius Feed Artery Ligation Surgery

Mice were prepared for surgery as with the Femoral Artery Ligation, except that hair was removed bilaterally from the dorsal aspect of the mouse. A skin incision was made parallel to the spine over the lateral edge of the spinotrapezius. The fat pad overlying the spinotrapezius was undermined using blunt dissection to expose the fat pad underlying the lateral edge of the muscle that contains the feed artery/vein pair. The artery was separated from the vein, and two single strands from 6-0 silk suture were used to ligate the artery, which was transected between the two sutures before closing the skin incision using 7-0 prolene suture. The sham surgery on the contralateral hindlimb included a skin incision and blunt dissection to expose the lateral artery-vein pair. In animals receiving either myogenic cells or vehicle, the spinotrapezius was undermined by gentle blunt dissection to create a 'pocket', as described above, between the ischemic and perfused arteriolar trees. For mice receiving thrombin, a positive control known to enhance collateral capillary arteriogenesis [8], 1 µL·g$^{-1}$ body weight of thrombin (1 NIH unit·µL$^{-1}$) was superfused superficially and injected deep to the muscle following ligation.

Maximal Collateral Diameter In Vivo—FIG. 2

Animals were anesthetized and prepared as described above, with hair also removed from the ventral aspects of neck. After moving to the surgical stage, the medial aspect of both hindlimbs was exposed with a skin incision and covered with plastic wrap to prevent desiccation. A second skin incision was made to expose the left jugular vein for the injection of fluorescein isothiocianate-conjugated dextran (FITC-dextran, 200,000 MW). Images of the maximum diameter of the midzone of the gracilis anterior collateral were captured using intravital microscopy (Olympus BXFM) with a 10× objective (Olympus LMPlan FL N) and digital imaging software (QCapture Pro) after electrical stimulation of the gracilis anterior muscle using parallel bipolar tungsten microelectrodes (FHC; Bowdoin, ME) delivering 1-2 mA square waves of 0.2 ms duration at 8 Hz for 90 seconds. This procedure was repeated on the contralateral hindlimb. Collateral diameters were measured in photomicrographs using Image/J.

Maximal Collateral Diameter In Vivo—FIG. 3

Animals were anesthetized and prepared as described above, without hair removal on the neck. A white LED was placed underneath the hindlimb and adjusted to allow transillumination of collateral vessels, which was supplemented with fiber-optic epi-illumination to improve contrast. Maximum collateral diameter was captured, as described above, after application of the vasodilators sodium nitroprusside ($10^{-4}$M) and adenosine ($10^{-4}$M) to both hindlimbs. Collateral diameters were measured in photomicrographs using Image/J.

Spinotrapezius Immunofluorescence

Perfusion Fixation

At 7 days following ligation, mice were perfusion fixed with 4% paraformaldehyde in preparation for immunofluorescence. Prior to fixation, overlying fascia was removed from the spinotrapezius muscles. Through a thoracotomy, a catheter was placed in the left ventricle, and 40 mL of vasodilator solution ($10^{-3}$ SNP, $10^{-4}$ adenosine, and 1 U·ml$^{-1}$ heparin in PBS) was perfused through the circulation at 2 ml·min$^{-1}$ using a syringe pump to displace the blood and maximally dilate the vasculature. Then, 5 mL of 4% paraformaldehyde (PFA) was perfused at 1 ml·min$^{-1}$ to fix the tissue. Following fixation, spinotrapezius muscles were undermined, resected, and underlying fascia was removed. Muscles were post-fixed overnight in 4% PFA at 4° C. and then transferred to PBS and stored at 4° C. until staining.

Staining and Imaging

To determine arterialized collateral capillary (ACC) diameter, the spinotrapezius muscles were stained with 1:200 1A4 clone alpha-smooth muscle actin to label smooth muscle cells (Cy3, Sigma-Aldrich 1 mg·mL$^{-1}$) and 1:20 Isolectin GS-IB4 from GRI (endothelial cells, Alexa Fluor 647, Thermo Fisher Scientific 1 mg·mL$^{-1}$). All stains were prepared in PBS with 0.1% Triton X-100 and 2% BSA, and incubated at 4° C. for 72 hours. The muscles were then washed 3 times for 20 minutes with 0.1% Triton X-100 in PBS, and then for 30 minutes in PBS. Muscles were mounted on glass slides in a 50:50 PBS:glycerol solution to clarify the skeletal muscle. Using a 20× objective on a confocal microscope (Olympus FV 1000, Olympus), three regions were imaged between ischemic and perfused arteriolar trees, where ACCs are located in operated muscle. To find the appropriate imaging area, the ischemic arteriolar tree was followed to a terminal arteriole where ACCs were identified because they are similar in appearance to capillaries, but they are also surrounded by smooth muscle cells. Unlike typical capillaries, ACCs connect two terminal arterioles, are relatively straight, and their long axis is parallel to the muscle fibers. On the sham side, the appropriate imaging location was found by following the arteriolar tree that arises from the lateral feed artery to a terminal arteriole until there was also a terminal arteriole from a different arteriolar tree in the field of view. At each location, a 150 µm thick z-stack with 5 µm thick slices was obtained. To measure diameter of diameter of capillaries and ACCs, the z-stacks were compressed and the channels were separated using Image/J. Inner diameters of alpha-smooth muscle actin positive vessels (ACCs) and lectin positive vessels (capillaries) were measured in a 200 µm$^2$ region in the compressed image.

Data Analysis

Differences maximum collateral diameter between mice with DIO and lean mice (FIG. 2) were determined by 1-way independent t-test. Differences in maximum collateral diameter in lean mice (FIG. 3) were determined by one-way ANOVA. Differences in maximum arterialized collateral capillary diameter in BALB/c mice were determined using one-way ANOVA and Tukey post hoc pairwise comparison.

Discussion

Given the poor prognosis for patients with Critical Limb Ischemia with currently available treatments [40], there is considerable interest in discovering methods to increase collateral arteriogenesis. Unfortunately, efforts to stimulate revascularization with cell transplantation have all appeared highly effective in animal studies [25] and small clinical trials [69] before failing in large, double-blind, randomized clinical trials [46]. Therefore, the results of the experiments described herein are surprising, in light of our research showing that satellite cells derived myoblasts appear to be the first known cell type to enhance arteriogenesis in mice with a compromised arteriogenesis response while having no effect on arteriogenesis in mice with a normal arteriogenesis response. The diverging responses between bone marrow-derived cells and myoblasts reflects that myoblasts are correlated with increasing maximum collateral artery diameter and enhancing arteriogenesis in the context of comorbidities common to patients with PAD, or in patients with genetically-deficient arteriogenesis responses.

REFERENCES

1. *REMINGTON'S PHARMACEUTICAL SCIENCES.* 18th ed. 1990, Easton, Pa.: Mack Publishing Co.
2. *The WHO Child Growth Standards.* [cited 2020 Apr. 14]; Available from: who.int/childgrowth/en/.
3. Adang M J, Brody M S, Cardineau G, Eagan N, Roush R T, Shewmaker C K, Jones A, Oakes J V, McBride K E, *The reconstruction and expression of a Bacillus thuringiensis cryIIIA gene in protoplasts and potato plants.* Plant Mol Biol, 1993. 21(6): p. 1131-45.
4. Aharinejad S, Abraham D, Paulus P, Zins K, Hofmann M, Michlits W, Gyongyosi M, Macfelda K, Lucas T, Trescher K, Grimm M, Stanley E R, *Colony-stimulating factor-1 transfection of myoblasts improves the repair of failing myocardium following autologous myoblast transplantation.* Cardiovasc Res, 2008. 79(3): p. 395-404.
5. Arnold L, Henry A, Poron F, Baba-Amer Y, van Rooijen N, Plonquet A, Gherardi R K, Chazaud B, *Inflammatory monocytes recruited after skeletal muscle injury switch into antiinflammatory macrophages to support myogenesis.* J Exp Med, 2007. 204(5): p. 1057-69.
6. Balestrieri M L, Lu S J, de Nigris F, Giovane A, Williams-Ignarro S, D'Armiento F P, Feng Q, Fiorito C, Testa G, Pastore L, Cacciatore F, Mancini F P, Servillo L, De Rosa G, Pagliarulo C, et al., *Therapeutic angiogenesis in diabetic apolipoprotein E-deficient mice using bone marrow cells, functional hemangioblasts and metabolic intervention.* Atherosclerosis, 2010. 209(2): p. 403-14.
7. Bambot S B, Russell A J, *Efficient total gene synthesis of 1.35-kb hybrid alpha-lytic protease gene using the polymerase chain reaction.* PCR Methods Appl, 1993. 2(3): p. 266-71.
8. Bruce A C, Peirce S M, *Exogenous thrombin delivery promotes collateral capillary arterialization and tissue reperfusion in the murine spinotrapezius muscle ischemia model.* Microcirculation, 2012. 19(2): p. 143-54.
9. Charge S B, Rudnicki M A, *Cellular and molecular regulation of muscle regeneration.* Physiol Rev, 2004. 84(1): p. 209-38.
10. Christov C, Chretien F, Abou-Khalil R, Bassez G, Vallet G, Authier F J, Bassaglia Y, Shinin V, Tajbakhsh S, Chazaud B, Gherardi R K, *Muscle satellite cells and endothelial cells: close neighbors and privileged partners.* Mol Biol Cell, 2007. 18(4): p. 1397-409.
11. Ciecierska A, Chodkowska K, Motyl T, Sadkowski T, *Myogenic cells applications in regeneration of post-infarction cardiac tissue.* J Physiol Pharmacol, 2013. 64(4): p. 401-8.
12. Clayton J A, Chalothorn D, Faber J E, *Vascular endothelial growth factor-A specifies formation of native collaterals and regulates collateral growth in ischemia.* Circ Res 2008. 103(9): p. 1027-36.
13. Dai X, Yan X, Zeng J, Chen J, Wang Y, Chen J, Li Y, Barati M T, Wintergerst K A, Pan K, Nystoriak M A, Conklin D J, Rokosh G, Epstein P N, Li X, et al., *Elevating CXCR7 Improves Angiogenic Function of EPCs via Akt/GSK-3beta/Fyn-Mediated Nrf2 Activation in Diabetic Limb Ischemia.* Circ Res, 2017. 120(5): p. e7-e23.
14. Della Vedova M C, Munoz M D, Santillan L D, Plateo-Pignatari M G, Germano M J, Rinaldi Tosi M E, Garcia S, Gomez N N, Fornes M W, Gomez Mejiba S E, Ramirez D C, *A Mouse Model of Diet-Induced Obesity Resembling Most Features of Human Metabolic Syndrome.* Nutr Metab Insights, 2016. 9: p. 93-102.
15. Ding Z, Huang H, *Mesenchymal stem cells in rabbit meniscus and bone marrow exhibit a similar feature but a heterogeneous multi-differentiation potential: superiority of meniscus as a cell source for meniscus repair.* BMC Musculoskelet Disord, 2015. 16: p. 65.
16. DiStasi M R, Mund J A, Bohlen H G, Miller S J, Ingram D A, Dalsing M C, Unthank J L, *Impaired compensation to femoral artery ligation in diet-induced obese mice is primarily mediated via suppression of collateral growth by Nox2 and p47phox.* Am J Physiol Heart Circ Physiol, 2015. 309(7): p. H1207-17.
17. Duff S, Mafilios M S, Bhounsule P, Hasegawa J T, *The burden of critical limb ischemia: a review of recent literature.* Vasc Health Risk Manag, 2019. 15: p. 187-208.
18. Fuchs E, Tumbar T, Guasch G, *Socializing with the neighbors: stem cells and their niche.* Cell, 2004. 116(6): p. 769-78.
19. He Y, Luo Y, Tang S, Rajantie I, Salven P, Heil M, Zhang R, Luo D, Li X, Chi H, Yu J, Carmeliet P, Schaper W, Sinusas A J, Sessa W C, et al., *Critical function of Bmx/Etk in ischemia-mediated arteriogenesis and angiogenesis.* J Clin Invest 2006. 116(9): p. 2344-55.
20. Heil M, Eitenmuller I, Schmitz-Rixen T, Schaper W, *Arteriogenesis versus angiogenesis: similarities and differences.* J Cell Mol Med 2006. 10(1): p. 45-55.
21. Heil M, Ziegelhoeffer T, Pipp F, Kostin S, Martin S, Clauss M, Schaper W, *Blood monocyte concentration is critical for enhancement of collateral artery growth.* Am J Physiol Heart Circ Physiol, 2002. 283(6): p. H2411-9.
22. Heuslein J L, Meisner J K, Li X, Song J, Vincentelli H, Leiphart R J, Ames E G, Blackman B R, Blackman B R, Price R J, *Mechanisms of Amplified Arteriogenesis in Collateral Artery Segments Exposed to Reversed Flow Direction.* Arterioscler Thromb Vasc Biol, 2015. 35(11): p. 2354-65.
23. Hirata K, Li T S, Nishida M, Ito H, Matsuzaki M, Kasaoka S, Hamano K, *Autologous bone marrow cell implantation as therapeutic angiogenesis for ischemic hindlimb in diabetic rat model.* Am J Physiol Heart Circ Physiol, 2003. 284(1): p. H66-70.
24. Horsley V, Jansen K M, Mills S T, Pavlath G K, *IL-4 acts as a myoblast recruitment factor during mammalian muscle growth.* Cell, 2003. 113(4): p. 483-94.
25. Hou L, Kim J J, Woo Y J, Huang N F, *Stem cell-based therapies to promote angiogenesis in ischemic cardiovascular disease.* Am J Physiol Heart Circ Physiol, 2016. 310(4): p. H455-65.
26. Innis M, Gelfand, D. and Sninsky, J., *PCR Applications: Protocols for Functional Genomics.* 1999, New York: Academic Press.
27. Innis M, Gelfand, D. and Sninsky, J., *PCR Strategies.* 1995, New York: Academic Press.
28. Jones D L, Wagers A J, *No place like home: anatomy and function of the stem cell niche.* Nat Rev Mol Cell Biol, 2008. 9(1): p. 11-21.

29. Jud Heinrichs C J, Virginia Ishler. *Body Condition Scoring as a Tool for Dairy Herd Management.* 2016 [cited 2020 Apr. 16]; Available from: extension.psu.edu/body-condition-scoring-as-a-tool-for-dairy-herd-management.
30. Kaul S, Jayaweera A R, *Determinants of microvascular flow.* Eur Heart J, 2006. 27(19): p. 2272-4.
31. Krishna S M, Omer S M, Golledge J, *Evaluation of the clinical relevance and limitations of current pre-clinical models of peripheral artery disease.* Clin Sci (Lond), 2016. 130(3): p. 127-50.
32. Lee J, Jun I, Park R I, Kang T J, Shin H, Cho S W, *Genetically engineered myoblast sheet for therapeutic angiogenesis.* Biomacromolecules, 2014. 15(1): p. 361-72.
33. Li T S, Furutani A, Takahashi M, Ohshima M, Qin S L, Kobayashi T, Ito H, Hamano K, *Impaired potency of bone marrow mononuclear cells for inducing therapeutic angiogenesis in obese diabetic rats.* Am J Physiol Heart Circ Physiol, 2006. 290(4): p. H1362-9.
34. Lotfi S, Patel A S, Mattock K, Egginton S, Smith A, Modarai B, *Towards a more relevant hind limb model of muscle ischaemia.* Atherosclerosis, 2013. 227(1): p. 1-8.
35. Madeddu P, Emanueli C, Spillmann F, Meloni M, Bouby N, Richer C, Alhenc-Gelas F, Van Weel V, Eefting D, Quax P H, Hu Y, Xu Q, Hemdahl A L, van Golde J, Huijberts M, et al., *Murine models of myocardial and limb ischemia: diagnostic end-points and relevance to clinical problems.* Vascul Pharmacol, 2006. 45(5): p. 281-301.
36. McDermott M M, Carr J, Liu K, Kramer C M, Yuan C, Tian L, Criqui M H, Guralnik J M, Ferrucci L, Zhao L, Xu D, Kibbe M, Berry J, Carroll T J, *Collateral vessel number, plaque burden, and functional decline in peripheral artery disease.* Vasc Med, 2014. 19(4): p. 281-288.
37. McDermott M M, Carroll T J, Kibbe M, Kramer C M, Liu K, Guralnik J M, Keeling A N, Criqui M H, Ferrucci L, Yuan C, Tian L, Liao Y, Berry J, Zhao L, Carr J, *Proximal superficial femoral artery occlusion, collateral vessels, and walking performance in peripheral artery disease.* JACC Cardiovasc Imaging, 2013. 6(6): p. 687-94.
38. Meligy F Y, Shigemura K, Behnsawy H M, Fujisawa M, Kawabata M, Shirakawa T, *The efficiency of in vitro isolation and myogenic differentiation of MSCs derived from adipose connective tissue, bone marrow, and skeletal muscle tissue.* In Vitro Cell Dev Biol Anim, 2012. 48(4): p. 203-15.
39. Nathoe H M, Koerselman J, Buskens E, van Dijk D, Stella P R, Plokker T H, Doevendans P A, Grobbee D E, de Jaegere P P, Octopus Study G, *Determinants and prognostic significance of collaterals in patients undergoing coronary revascularization.* Am J Cardiol, 2006. 98(1): p. 31-5.
40. Norgren L, Hiatt W R, Dormandy J A, Nehler M R, Harris K A, Fowkes F G, Group T I W, *Inter-Society Consensus for the Management of Peripheral Arterial Disease (TASC II).* J Vasc Surg, 2007. 45 Suppl S: p. S5-67.
41. Okeke E, Dokun A O, *Role of genetics in peripheral arterial disease outcomes; significance of limb-salvage quantitative locus-1 genes.* Exp Biol Med (Maywood), 2018. 243(2): p. 190-197.
42. Palmieri B, Tremblay J P, Daniele L, *Past, present and future of myoblast transplantation in the treatment of Duchenne muscular dystrophy.* Pediatr Transplant, 2010. 14(7): p. 813-9.
43. Patsalos A, Pap A, Varga T, Trencsenyi G, Contreras G A, Garai I, Papp Z, Derso B, Pintye E, Nagy L, *In situ macrophage phenotypic transition is affected by altered cellular composition prior to acute sterile muscle injury.* J Physiol, 2017. 595(17): p. 5815-5842.
44. Peeters Weem S M, Teraa M, de Borst G J, Verhaar M C, Moll F L, *Bone Marrow derived Cell Therapy in Critical Limb Ischemia: A Meta-analysis of Randomized Placebo Controlled Trials.* Eur J Vasc Endovasc Surg, 2015. 50(6): p. 775-83.
45. Perez-Castellano N, Garcia E J, Abeytua M, Soriano J, Serrano J A, Elizaga J, Botas J, Lopez-Sendon J L, Delcan J L, *Influence of collateral circulation on in-hospital death from anterior acute myocardial infarction.* J Am Coll Cardiol, 1998. 31(3): p. 512-8.
46. Perin E C, Murphy M P, March K L, Bolli R, Loughran J, Yang P C, Leeper N J, Dalman R L, Alexander J, Henry T D, Traverse J H, Pepine C J, Anderson R D, Berceli S, Willerson J T, et al., *Evaluation of Cell Therapy on Exercise Performance and Limb Perfusion in Peripheral Artery Disease: The CCTRN PACE Trial (Patients With Intermittent Claudication Injected With ALDH Bright Cells).* Circulation, 2017. 135(15): p. 1417-1428.
47. Peterson C M, Thomas D M, Blackburn G L, Heymsfield S B, *Universal equation for estimating ideal body weight and body weight at any BMI.* Am J Clin Nutr, 2016. 103(5): p. 1197-203.
48. Rhoads R P, Flann K L, Cardinal T R, Rathbone C R, Liu X, Allen R E, *Satellite cells isolated from aged or dystrophic muscle exhibit a reduced capacity to promote angiogenesis in vitro.* Biochem Biophys Res Commun, 2013. 440(3): p. 399-404.
49. Rhoads R P, Johnson R M, Rathbone C R, Liu X, Temm-Grove C, Sheehan S M, Hoying J B, Allen R E, *Satellite cell-mediated angiogenesis in vitro coincides with a functional hypoxia-inducible factor pathway.* Am J Physiol Cell Physiol, 2009. 296(6): p. C1321-8.
50. Rigato M, Monami M, Fadini G P, *Autologous Cell Therapy for Peripheral Arterial Disease: Systematic Review and Meta-Analysis of Randomized, Nonrandomized, and Noncontrolled Studies.* Circ Res, 2017. 120(8): p. 1326-1340.
51. Rong S L, Wang X L, Zhang C Y, Song Z H, Cui L H, He X F, Li X J, Du H J, Li B, *Transplantation of HGF gene-engineered skeletal myoblasts improve infarction recovery in a rat myocardial ischemia model.* PLoS One, 2017. 12(5): p. e0175807.
52. Sabia R I, Powers E R, Ragosta M, Sarembock L I, Burwell L R, Kaul S, *An association between collateral blood flow and myocardial viability in patients with recent myocardial infarction.* N Engl J Med, 1992. 327(26): p. 1825-31.
53. Saclier M, Cuvellier S, Magnan M, Mounier R, Chazaud B, *Monocyte/macrophage interactions with myogenic precursor cells during skeletal muscle regeneration.* FEBS J, 2013. 280(17): p. 4118-30.
54. Sambrook J, Fritsch, E. F. and Maniatis, T., *Molecular Cloning: A Laboratory Manual.* 3rd ed. 2001, Plainview, N.Y.: Cold Spring Harbor Laboratory Press.
55. S F G, *Developmental Biology.* 6th ed. 2000, Sunderland, MA: Sinauer Associates.
56. Shen Y, Ding F H, Dai Y, Wang X Q, Zhang R Y, Lu L, Shen W F, *Reduced coronary collateralization in type 2 diabetic patients with chronic total occlusion.* Cardiovasc Diabetol, 2018. 17(1): p. 26.

57. Snijders T, Nederveen J P, McKay B R, Joanisse S, Verdijk L B, van Loon U, Parise G, *Satellite cells in human skeletal muscle plasticity*. Front Physiol, 2015. 6: p. 283.
58. Takeda K, Fukumoto S, Motoyama K, Morioka T, Mori K, Kageyama K, Sakai Y, Sato H, Suzuki M, Koyama H, Shoji T, Ishimura E, Emoto M, Furuzono T, Nakajima K, et al., *Injectable cell scaffold restores impaired cell-based therapeutic angiogenesis in diabetic mice with hindlimb ischemia*. Biochem Biophys Res Commun, 2014. 454(1): p. 119-24.
59. Taylor J C, Yang H T, Laughlin M H, Terjung R L, *Alpha-adrenergic and neuropeptide Y Y1 receptor control of collateral circuit conductance: influence of exercise training*. J Physiol 2008. 586(Pt 24): p. 5983-98.
60. Tirziu D, Moodie K L, Zhuang Z W, Singer K, Helisch A, Dunn J F, Li W, Singh J, Simons M, *Delayed arteriogenesis in hypercholesterolemic mice*. Circulation, 2005. 112(16): p. 2501-9.
61. van Golde J M, Ruiter M S, Schaper N C, Voo S, Waltenberger J, Backes W H, Post M J, Huijberts M S, *Impaired collateral recruitment and outward remodeling in experimental diabetes*. Diabetes, 2008. 57(10): p. 2818-23.
62. van Weel V, de Vries M, Voshol P J, Verloop R E, Eilers P H, van Hinsbergh V W, van Bockel J H, Quax P H, *Hypercholesterolemia reduces collateral artery growth more dominantly than hyperglycemia or insulin resistance in mice*. Arteriosclerosis, Thrombosis, and Vascular Biology, 2006. 26(6): p. 1383-90.
63. Vinarov A, Atala A, Yoo J, Slusarenco R, Zhumataev M, Zhito A, Butnaru D, *Cell therapy for stress urinary incontinence: Present-day frontiers*. J Tissue Eng Regen Med, 2018. 12(2): p. e1108-e1121.
64. Vincent K A, Jiang C, Boltje I, Kelly R A, *Gene therapy progress and prospects: therapeutic angiogenesis for ischemic cardiovascular disease*. Gene Ther., 2007. 14(10): p. 781-789.
65. Virani S S, Alonso A, Benjamin E J, Bittencourt M S, Callaway C W, Carson A P, Chamberlain A M, Chang A R, Cheng S, Delling F N, Djousse L, Elkind M S V, Ferguson J F, Fornage M, Khan S S, et al., *Heart Disease and Stroke Statistics—2020 Update: A Report From the American Heart Association*. Circulation, 2020. 141(9): p. e139-e596.
66. Wang S, Zhang H, Dai X, Sealock R, Faber J E, *Genetic architecture underlying variation in extent and remodeling of the collateral circulation*. Circulation Research, 2010. 107(4): p. 558-68.
67. Wang S, Zhang H, Wiltshire T, Sealock R, Faber J E, *Genetic dissection of the Canq1 locus governing variation in extent of the collateral circulation*. PLoS One, 2012. 7(3): p. e31910.
68. Welcome A. *Definition of Obesity*. 2017 [cited 2020 Apr. 13]; Available from: obesitymedicine.org/definition-of-obesity/.
69. Xie B, Luo H, Zhang Y, Wang Q, Zhou C, Xu D, *Autologous Stem Cell Therapy in Critical Limb Ischemia: A Meta-Analysis of Randomized Controlled Trials*. Stem Cells Int, 2018. 2018: p. 7528464.
70. Yablonka-Reuveni Z, *The skeletal muscle satellite cell: still young and fascinating at 50*. J Histochem Cytochem, 2011. 59(12): p. 1041-59.
71. Yao Y, Li Y, Song Q, Hu C, Xie W, Xu C, Chen Q, Wang Q K, *Angiogenic Factor AGGF1-Primed Endothelial Progenitor Cells Repair Vascular Defect in Diabetic Mice*. Diabetes, 2019. 68(8): p. 1635-1648.
72. Yu J, Demuinck E D, Zhuang Z, Drinane M, Kauser K, Rubanyi G M, Qian H S, Murata T, Escalante B, Sessa W C, *Endothelial nitric oxide synthase is critical for ischemic remodeling, mural cell recruitment, and blood flow reserve*. Proc.Natl.Acad.Sci.U.S.A, 2005. 102(31): p. 10999-11004.
73. Yu P, Li Q, Liu Y, Zhang J, Seldeen K, Pang M, *Pro-angiogenic efficacy of transplanting endothelial progenitor cells for treating hindlimb ischemia in hyperglycemic rabbits*. J Diabetes Complications, 2015. 29(1): p. 13-9.

What is claimed is:

1. A method of increasing maximum collateral diameter of at least one collateral of an animal, comprising,
    a) administering to said animal satellite cell derived myoblasts; and
    b) increasing maximum collateral diameter of said at least one collateral, wherein said animal is obese.

2. The method of claim 1, further comprising calculating the body fat of said animal to identify the animal as obese and/or analyzing a sample from said animal to identify the animal as having a genetic alteration resulting in a phenotype of impaired arteriogenesis.

3. The method of claim 1, wherein maximum collateral diameter of said at least one collateral is increased by up to 32%.

4. The method of claim 1, wherein maximum collateral diameter of said at least one collateral is increased by at least 30%.

5. The method of claim 1, wherein blood flow is increased by up to 200%.

6. The method of claim 1, wherein blood flow is increased by at least 200%.

7. The method of claim 1, wherein said animal has a genetic modification at the Canq1 locus or the LSq-1 locus.

8. The method of claim 1, wherein the maximum collateral diameter is increased and wherein the myoblast is not altered genetically nor chemically to produce an angiogenic factor.

9. The method of claim 1, wherein said administration of said satellite cell derived myoblasts comprises transplanting said satellite cell derived myoblasts into said animal.

10. The method of claim 1, wherein said administration of said satellite cell derived myoblasts comprises transplanting said satellite cell derived myoblasts into muscle of said animal comprising said at least one collateral.

11. The method of claim 1, wherein said animal has ischemia and said ischemia is reduced after introduction of said satellite cell derived myoblasts.

12. The method of claim 1, further comprising calculating the body fat of said animal to identify the animal as obese and/or analyzing a sample from said animal to identify the animal as having a genetic alteration resulting in a phenotype of impaired arteriogenesis and increasing maximum collateral diameter of said at least one collateral by at least 30% and increasing blood flow by at least 200%.

13. A method of reducing ischemia in an obese animal or animal having a genetic alteration causing impaired arteriogenesis, comprising,
    a) introducing into said animal satellite cell derived myoblasts;
    b) increasing maximum diameter of said at least one collateral, wherein the at least one collateral is a collateral of a peripheral artery; and
    c) reducing ischemia in said animal;
    wherein said animal is obese.

14. The method of claim 12, wherein said ischemia results from arterial occlusion in said animal.

15. The method of claim 12, wherein damage to tissue of said animal is decreased compared to an obese animal or animal having a genetic alteration resulting in a phenotype of impaired angiogenesis that is not administered said satellite derived myoblasts.

16. The method of claim 12, wherein maximum diameter of said at least one collateral is increased by at least 30%.

17. The method of claim 16, further comprising calculating the body fat of said animal to identify the animal as obese and/or analyzing a sample from said animal to identify the animal as having a genetic alteration causing impaired arteriogenesis.

18. The method of claim 12, wherein blood flow of said collateral is increased by at least 200%.

19. A method of treating peripheral artery disease in an animal, the method comprising,
   a) administering to said animal satellite cell derived myoblasts; and
   b) increasing maximum collateral diameter of at least one collateral, wherein the at least one collateral is a collateral of a peripheral artery;
   wherein said animal is obese.

* * * * *